US009952242B2

(12) United States Patent
Riether

(10) Patent No.: US 9,952,242 B2
(45) Date of Patent: Apr. 24, 2018

(54) LABORATORY SAMPLE DISTRIBUTION SYSTEM AND LABORATORY AUTOMATION SYSTEM

(71) Applicant: Roche Diagnostics Operations, Inc., Indianapolis, IN (US)

(72) Inventor: Christian Riether, Muehltal (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 14/843,418

(22) Filed: Sep. 2, 2015

(65) Prior Publication Data

US 2016/0077120 A1 Mar. 17, 2016

(30) Foreign Application Priority Data

Sep. 12, 2014 (EP) .................................. 14184623

(51) Int. Cl.
| | |
|---|---|
| *G01N 35/04* | (2006.01) |
| *B66C 19/00* | (2006.01) |
| *B65G 54/02* | (2006.01) |
| *B65G 37/00* | (2006.01) |

(52) U.S. Cl.
CPC ............. *G01N 35/04* (2013.01); *B65G 37/00* (2013.01); *B65G 54/02* (2013.01); *B66C 19/005* (2013.01); *G01N 2035/0406* (2013.01); *G01N 2035/0477* (2013.01); *G01N 2035/0494* (2013.01)

(58) Field of Classification Search
CPC ........... G01N 35/04; G01N 2035/0406; G01N 2035/0477; G01N 2035/0494; B65G 37/00; B65G 54/02; B66C 19/005
See application file for complete search history.

(56) References Cited

U.S. PATENT DOCUMENTS

| | | |
|---|---|---|
| 3,273,727 A | 9/1966 | Rogers et al. |
| 3,653,485 A | 4/1972 | Donlon |
| 3,901,656 A | 8/1975 | Durkos et al. |
| 4,150,666 A | 4/1979 | Brush |
| 4,395,164 A | 7/1983 | Beltrop |
| 4,544,068 A | 10/1985 | Cohen |
| 4,771,237 A | 9/1988 | Daley |
| 5,120,506 A | 6/1992 | Saito et al. |
| 5,295,570 A | 3/1994 | Grecksch et al. |
| 5,309,049 A | 5/1994 | Kawada et al. |
| 5,523,131 A | 6/1996 | Isaacs et al. |
| 5,530,345 A | 6/1996 | Murari et al. |
| 5,636,548 A | 6/1997 | Dunn et al. |
| 5,641,054 A | 6/1997 | Mori et al. |

(Continued)

FOREIGN PATENT DOCUMENTS

| | | | | |
|---|---|---|---|---|
| CH | WO 2013064662 A1 | * | 5/2013 | ............. B65G 54/02 |
| CN | 201045617 Y | | 4/2008 | |

(Continued)

*Primary Examiner* — Benjamin R Whatley
(74) *Attorney, Agent, or Firm* — Roche Diagnostics Operations, Inc.

(57) ABSTRACT

A laboratory sample distribution system having a recovery device and a laboratory automation system having such a laboratory sample distribution system are presented. The recovery device is adapted to manipulate items such as sample container carriers or sample containers on a transport plane of the laboratory sample distribution system in the case of an error condition.

12 Claims, 2 Drawing Sheets

(56) References Cited

U.S. PATENT DOCUMENTS

| | | | |
|---|---|---|---|
| 5,651,941 A | 7/1997 | Stark et al. | |
| 5,720,377 A | 2/1998 | Lapeus et al. | |
| 5,735,387 A * | 4/1998 | Polaniec | G01N 35/04 198/465.1 |
| 5,788,929 A | 8/1998 | Nesti | |
| 6,045,319 A | 4/2000 | Uchida et al. | |
| 6,062,398 A | 5/2000 | Talmayr | |
| 6,141,602 A | 10/2000 | Igarashi et al. | |
| 6,151,535 A | 11/2000 | Ehlers | |
| 6,184,596 B1 | 2/2001 | Ohzeki | |
| 6,191,507 B1 | 2/2001 | Peltier et al. | |
| 6,206,176 B1 | 3/2001 | Blonigan et al. | |
| 6,255,614 B1 * | 7/2001 | Yamakawa | G01N 35/04 209/509 |
| 6,260,360 B1 | 7/2001 | Wheeler | |
| 6,279,728 B1 | 8/2001 | Jung et al. | |
| 6,293,750 B1 | 9/2001 | Cohen et al. | |
| 6,429,016 B1 | 8/2002 | McNeil | |
| 6,444,171 B1 | 9/2002 | Sakazume et al. | |
| 6,571,934 B1 | 6/2003 | Thompson et al. | |
| 7,028,831 B2 | 4/2006 | Veiner | |
| 7,078,082 B2 | 7/2006 | Adams | |
| 7,122,158 B2 | 10/2006 | Itoh | |
| 7,278,532 B2 | 10/2007 | Martin | |
| 7,326,565 B2 | 2/2008 | Yokoi et al. | |
| 7,425,305 B2 | 9/2008 | Itoh | |
| 7,428,957 B2 | 9/2008 | Schaefer | |
| 7,578,383 B2 | 8/2009 | Itoh | |
| 7,597,187 B2 | 10/2009 | Bausenwein et al. | |
| 7,850,914 B2 | 12/2010 | Veiner et al. | |
| 7,858,033 B2 | 12/2010 | Itoh | |
| 7,875,254 B2 | 1/2011 | Garton et al. | |
| 7,939,484 B1 | 5/2011 | Loeffler et al. | |
| 8,240,460 B1 | 8/2012 | Bleau et al. | |
| 8,281,888 B2 | 10/2012 | Bergmann | |
| 8,502,422 B2 | 8/2013 | Lykkegaard | |
| 8,796,186 B2 | 8/2014 | Shirazi | |
| 9,211,543 B2 | 12/2015 | Ohga et al. | |
| 9,239,335 B2 | 1/2016 | Heise et al. | |
| 2002/0009391 A1 | 1/2002 | Marquiss et al. | |
| 2003/0089581 A1 | 5/2003 | Thompson et al. | |
| 2003/0092185 A1 | 5/2003 | Qureshi et al. | |
| 2004/0050836 A1 | 3/2004 | Nesbitt et al. | |
| 2004/0084531 A1 | 5/2004 | Itoh | |
| 2005/0061622 A1 | 3/2005 | Martin | |
| 2005/0109580 A1 | 5/2005 | Thompson | |
| 2005/0194333 A1 | 9/2005 | Veiner et al. | |
| 2005/0196320 A1 | 9/2005 | Veiner et al. | |
| 2005/0226770 A1 | 10/2005 | Allen et al. | |
| 2005/0242963 A1 | 11/2005 | Oldham et al. | |
| 2005/0247790 A1 | 11/2005 | Itoh | |
| 2005/0260101 A1 | 11/2005 | Nauck et al. | |
| 2005/0271555 A1 | 12/2005 | Itoh | |
| 2006/0000296 A1 | 1/2006 | Salter | |
| 2006/0047303 A1 | 3/2006 | Ortiz et al. | |
| 2006/0219524 A1 | 10/2006 | Kelly et al. | |
| 2007/0116611 A1 | 5/2007 | DeMarco | |
| 2007/0210090 A1 | 9/2007 | Sixt et al. | |
| 2007/0248496 A1 | 10/2007 | Bondioli et al. | |
| 2007/0276558 A1 | 11/2007 | Kim | |
| 2008/0012511 A1 | 1/2008 | Ono | |
| 2008/0029368 A1 | 2/2008 | Komori | |
| 2008/0056328 A1 | 3/2008 | Rund et al. | |
| 2008/0131961 A1 | 6/2008 | Crees et al. | |
| 2008/0286162 A1 | 11/2008 | Onizawa et al. | |
| 2009/0004732 A1 | 1/2009 | LaBarre et al. | |
| 2009/0022625 A1 | 1/2009 | Lee et al. | |
| 2009/0081771 A1 | 3/2009 | Breidford et al. | |
| 2009/0128139 A1 | 5/2009 | Drenth et al. | |
| 2009/0142844 A1 * | 6/2009 | Le Comte | G01N 35/00594 436/8 |
| 2009/0180931 A1 | 7/2009 | Silbert et al. | |
| 2009/0322486 A1 | 12/2009 | Gerstel | |
| 2010/0000250 A1 | 1/2010 | Sixt | |
| 2010/0152895 A1 | 6/2010 | Dai | |
| 2010/0175943 A1 | 7/2010 | Bergmann | |
| 2010/0186618 A1 | 7/2010 | King et al. | |
| 2010/0255529 A1 * | 10/2010 | Cocola | C12Q 1/04 435/34 |
| 2010/0300831 A1 | 12/2010 | Pedrazzini | |
| 2010/0312379 A1 | 12/2010 | Pedrazzini | |
| 2011/0050213 A1 | 3/2011 | Furukawa | |
| 2011/0124038 A1 | 5/2011 | Bishop et al. | |
| 2011/0172128 A1 | 7/2011 | Davies et al. | |
| 2011/0186406 A1 | 8/2011 | Kraus et al. | |
| 2011/0287447 A1 | 11/2011 | Norderhaug et al. | |
| 2012/0037696 A1 | 2/2012 | Lavi | |
| 2012/0129673 A1 | 5/2012 | Fukugaki et al. | |
| 2012/0178170 A1 | 7/2012 | Van Praet | |
| 2012/0211645 A1 | 8/2012 | Tullo et al. | |
| 2012/0275885 A1 | 11/2012 | Furrer et al. | |
| 2012/0282683 A1 | 11/2012 | Mototsu | |
| 2012/0295358 A1 | 11/2012 | Ariff et al. | |
| 2012/0310401 A1 | 12/2012 | Shah | |
| 2013/0034410 A1 * | 2/2013 | Heise | B65G 54/02 414/222.13 |
| 2013/0126302 A1 | 5/2013 | Johns et al. | |
| 2013/0153677 A1 | 6/2013 | Leen et al. | |
| 2013/0180824 A1 | 7/2013 | Kleinikkink et al. | |
| 2013/0263622 A1 | 10/2013 | Mullen et al. | |
| 2013/0322992 A1 | 12/2013 | Pedrazzini | |
| 2014/0170023 A1 | 6/2014 | Saito et al. | |
| 2014/0231217 A1 | 8/2014 | Denninger et al. | |
| 2014/0234065 A1 | 8/2014 | Heise et al. | |
| 2014/0234949 A1 * | 8/2014 | Wasson | G01N 35/1065 435/287.2 |
| 2014/0234978 A1 * | 8/2014 | Heise | B65G 54/02 436/48 |
| 2015/0014125 A1 | 1/2015 | Hecht | |
| 2015/0233956 A1 | 8/2015 | Buehr | |
| 2015/0233957 A1 | 8/2015 | Riether | |
| 2015/0241457 A1 | 8/2015 | Miller | |
| 2015/0273468 A1 | 10/2015 | Croquette et al. | |
| 2015/0273691 A1 | 10/2015 | Pollack | |
| 2015/0276775 A1 * | 10/2015 | Mellars | G01N 35/0092 436/501 |
| 2015/0276776 A1 | 10/2015 | Riether | |
| 2015/0276777 A1 | 10/2015 | Riether et al. | |
| 2015/0276778 A1 | 10/2015 | Riether et al. | |
| 2015/0276781 A1 | 10/2015 | Riether et al. | |
| 2015/0276782 A1 | 10/2015 | Riether | |
| 2015/0360876 A1 | 12/2015 | Sinz | |
| 2015/0360878 A1 | 12/2015 | Denninger et al. | |
| 2016/0003859 A1 | 1/2016 | Wenczel et al. | |
| 2016/0025756 A1 * | 1/2016 | Pollack | G01N 35/04 436/47 |
| 2016/0054341 A1 | 2/2016 | Edelmann | |
| 2016/0054344 A1 | 2/2016 | Heise et al. | |
| 2016/0069715 A1 | 3/2016 | Sinz | |
| 2016/0097786 A1 | 4/2016 | Malinowski et al. | |
| 2016/0229565 A1 | 8/2016 | Margner | |
| 2016/0274137 A1 | 9/2016 | Baer | |
| 2016/0282378 A1 | 9/2016 | Malinowski et al. | |
| 2016/0341750 A1 | 11/2016 | Sinz et al. | |
| 2016/0341751 A1 | 11/2016 | Huber et al. | |
| 2017/0059599 A1 | 3/2017 | Riether | |
| 2017/0096307 A1 | 4/2017 | Mahmudimanesh et al. | |
| 2017/0097372 A1 | 4/2017 | Heise et al. | |
| 2017/0101277 A1 | 4/2017 | Malinowski | |
| 2017/0108522 A1 | 4/2017 | Baer | |
| 2017/0131307 A1 | 5/2017 | Pedain | |
| 2017/0131309 A1 | 5/2017 | Pedain | |
| 2017/0131310 A1 | 5/2017 | Volz et al. | |
| 2017/0138971 A1 | 5/2017 | Heise et al. | |
| 2017/0160299 A1 | 6/2017 | Schneider et al. | |
| 2017/0168079 A1 | 6/2017 | Sinz | |
| 2017/0174448 A1 | 6/2017 | Sinz | |
| 2017/0184622 A1 | 6/2017 | Sinz et al. | |
| 2017/0248623 A1 | 8/2017 | Kaeppeli et al. | |
| 2017/0248624 A1 | 8/2017 | Kaeppeli et al. | |
| 2017/0363608 A1 | 12/2017 | Sinz | |

(56) References Cited

U.S. PATENT DOCUMENTS

FOREIGN PATENT DOCUMENTS

| | | | |
|---|---|---|---|
| CN | 102109530 A | 6/2011 |
| DE | 3909786 A1 | 9/1990 |
| DE | 102012000665 A1 | 8/2012 |
| DE | 102011090044 A1 | 7/2013 |
| EP | 0601213 A1 | 10/1992 |
| EP | 0775650 A1 | 5/1997 |
| EP | 0896936 A1 | 2/1999 |
| EP | 0916406 A2 | 5/1999 |
| EP | 1122194 A1 | 8/2001 |
| EP | 1524525 A1 | 4/2005 |
| EP | 2119643 A1 | 11/2009 |
| EP | 2148117 A1 | 1/2010 |
| EP | 2327646 A1 | 6/2011 |
| EP | 2447701 A2 | 5/2012 |
| EP | 2500871 A1 | 9/2012 |
| EP | 2502675 A1 | 9/2012 |
| EP | 2887071 A1 | 6/2015 |
| GB | 2165516 A | 4/1986 |
| JP | S56-147209 A | 11/1981 |
| JP | 60-223481 A | 11/1985 |
| JP | 61-081323 A | 4/1986 |
| JP | S61-069604 A | 4/1986 |
| JP | S61-094925 A | 5/1986 |
| JP | S61-174031 A | 8/1986 |
| JP | S61-217434 A | 9/1986 |
| JP | S62-100161 A | 5/1987 |
| JP | S63-31918 A | 2/1988 |
| JP | S63-48169 A | 2/1988 |
| JP | S63-82433 U | 5/1988 |
| JP | S63-290101 A | 11/1988 |
| JP | 01-148966 A | 6/1989 |
| JP | 1148966 A | 6/1989 |
| JP | 01-266860 A | 10/1989 |
| JP | H01-266860 A | 10/1989 |
| JP | H02-87903 A | 3/1990 |
| JP | 03-192013 A | 8/1991 |
| JP | H03-38704 Y2 | 8/1991 |
| JP | H04-127063 A | 4/1992 |
| JP | H05-69350 A | 3/1993 |
| JP | H05-69350 A2 | 3/1993 |
| JP | H05-142232 A | 6/1993 |
| JP | H05-180847 A | 7/1993 |
| JP | 06-26806 A | 2/1994 |
| JP | 06-26808 A | 4/1994 |
| JP | 06-148198 A | 5/1994 |
| JP | H06-148198 A | 5/1994 |
| JP | 6-156730 A | 6/1994 |
| JP | 06-211306 A | 8/1994 |
| JP | 07-228345 A | 8/1995 |
| JP | 07-236838 A | 9/1995 |
| JP | H07-301637 A | 11/1995 |
| JP | H09-17848 A | 1/1997 |
| JP | H11-083865 A | 3/1999 |
| JP | H11-083865 A | 3/1999 |
| JP | H11-264828 A | 9/1999 |
| JP | H11-264828 A | 9/1999 |
| JP | H11-304812 A | 11/1999 |
| JP | H11-326336 A | 11/1999 |
| JP | H11-326336 A | 11/1999 |
| JP | 2000-105243 A | 4/2000 |
| JP | 2000-105246 A | 4/2000 |
| JP | 3112393 A | 9/2000 |
| JP | 2001-124786 A | 5/2001 |
| JP | 2001-124786 A1 | 5/2001 |
| JP | 2001-240245 A | 9/2001 |
| JP | 2005-001055 A | 1/2005 |
| JP | 2005-249740 A | 9/2005 |
| JP | 2006-106008 A | 4/2006 |
| JP | 2007-309675 A | 11/2007 |
| JP | 2007-314262 A | 12/2007 |
| JP | 2007-322289 A | 12/2007 |
| JP | 2009-036643 A | 2/2009 |
| JP | 2009-062188 A | 3/2009 |
| JP | 2009-145188 A | 7/2009 |
| JP | 2009-300402 A | 12/2009 |
| JP | 2010-243310 A | 10/2010 |
| JP | 2013-172009 A | 9/2013 |
| JP | 2013-190400 A | 9/2013 |
| SU | 685591 A1 | 9/1979 |
| WO | 96/36437 A1 | 11/1996 |
| WO | 03/042048 A3 | 5/2003 |
| WO | 2007/024540 A1 | 3/2007 |
| WO | 2008/133708 A1 | 11/2008 |
| WO | 2009/002358 A1 | 12/2008 |
| WO | 2010/042722 A1 | 4/2010 |
| WO | 2010/087303 A1 | 8/2010 |
| WO | 2010/129715 A1 | 11/2010 |
| WO | 2011/138448 A1 | 11/2011 |
| WO | 2012/158520 A1 | 11/2012 |
| WO | 2012/158541 A1 | 11/2012 |
| WO | 2012/170636 A1 | 12/2012 |
| WO | 2013/152089 A1 | 10/2013 |
| WO | 2013/169778 A1 | 11/2013 |
| WO | 2013/177163 A1 | 11/2013 |
| WO | 2014/059134 A1 | 4/2014 |
| WO | 2014/159134 A1 | 4/2014 |
| WO | 2014/071214 A1 | 5/2014 |

* cited by examiner

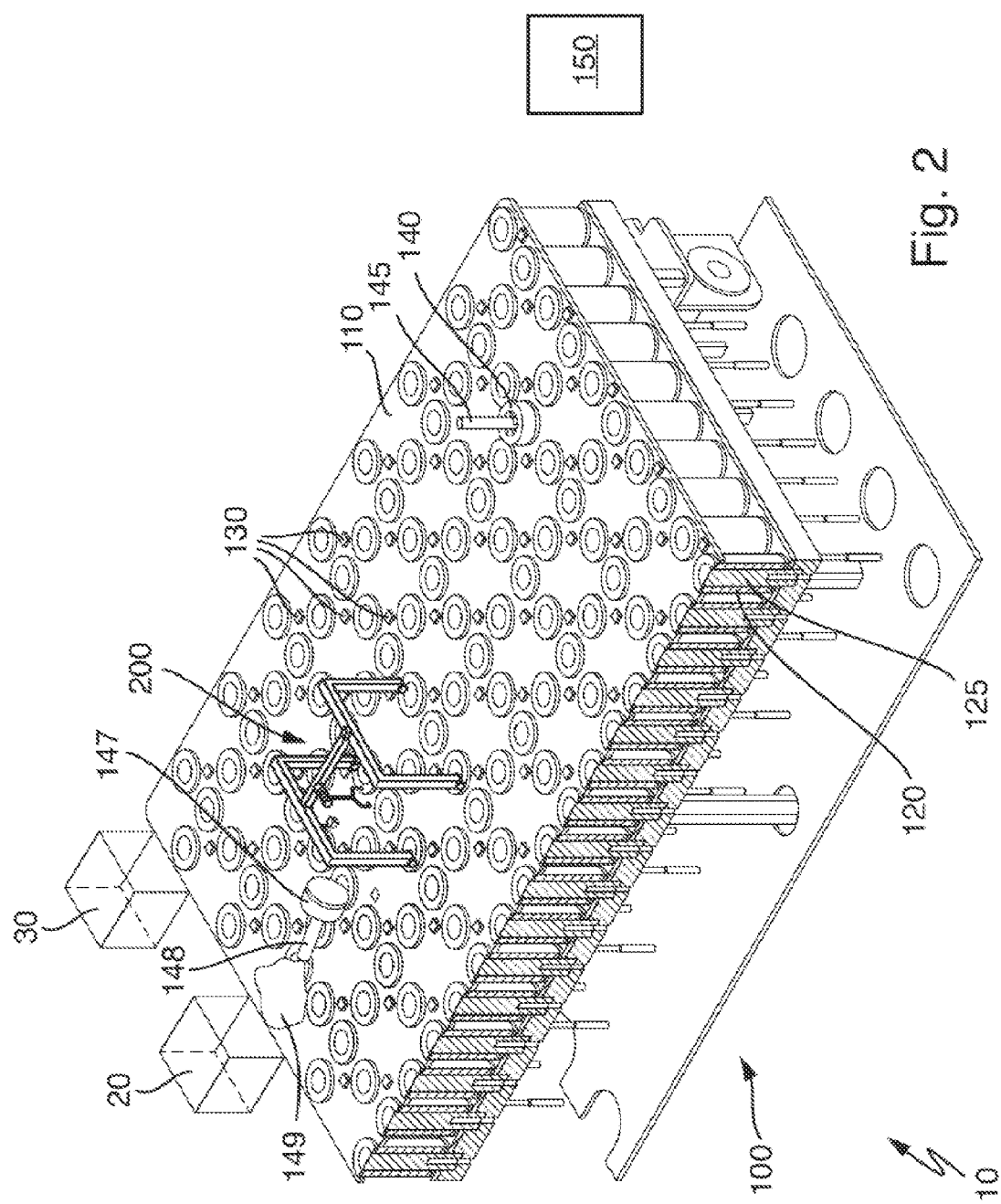

LABORATORY SAMPLE DISTRIBUTION SYSTEM AND LABORATORY AUTOMATION SYSTEM

CROSS-REFERENCE TO RELATED APPLICATIONS

This application claims priority to EP 14184623.8, filed Sep. 12, 2014, which is hereby incorporated by reference.

BACKGROUND

The present disclosure generally relates to a laboratory sample distribution system and to a laboratory automation system comprising such a laboratory sample distribution system.

Laboratory sample distribution systems can be used to transport samples between laboratory stations. A laboratory sample distribution system together with such laboratory stations can be denoted as a laboratory automation system.

A typical laboratory sample distribution system can have a plurality of sample container carriers arranged on a transport plane in order to carry sample containers. Such laboratory sample distribution systems are typically used for medical samples, wherein it is important that samples are not subject to contamination while being analyzed or while being transported on the transport plane.

However, laboratory sample distribution systems are complex, technical systems that can show error conditions in exceptional cases, for example, at occurrence of an earthquake. If manual action is required in order to bring the laboratory sample distribution system in a condition for further operation, the risk to contaminate samples and/or operating personal is high.

Therefore, there is a need for a laboratory sample distribution system that minimizes the need for manual action.

SUMMARY

According to the present disclosure, a laboratory sample distribution system is presented. The laboratory sample distribution system can comprise a plurality of sample container carriers to carry one or more sample containers, a transport plane to support the sample container carriers, a movement device to move a sample container carrier on top of the transport plane, a control device to control the movement of the sample container carriers on top of the transport plane by controlling the movement device such that the sample container carriers move along corresponding transport paths, and a recovery device. The recovery device can comprise a handler to handle a sample container carrier or a sample container, and a drive to move the recovery device on top of the transport plane.

Accordingly, it is a feature of the embodiments of the present disclosure to provide a laboratory sample distribution system that minimizes the need for manual action. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which:

FIG. 2 illustrates schematically shows a laboratory automation system comprising a laboratory sample distribution system according to an embodiment of the present disclosure.

DETAILED DESCRIPTION

Figure 1:
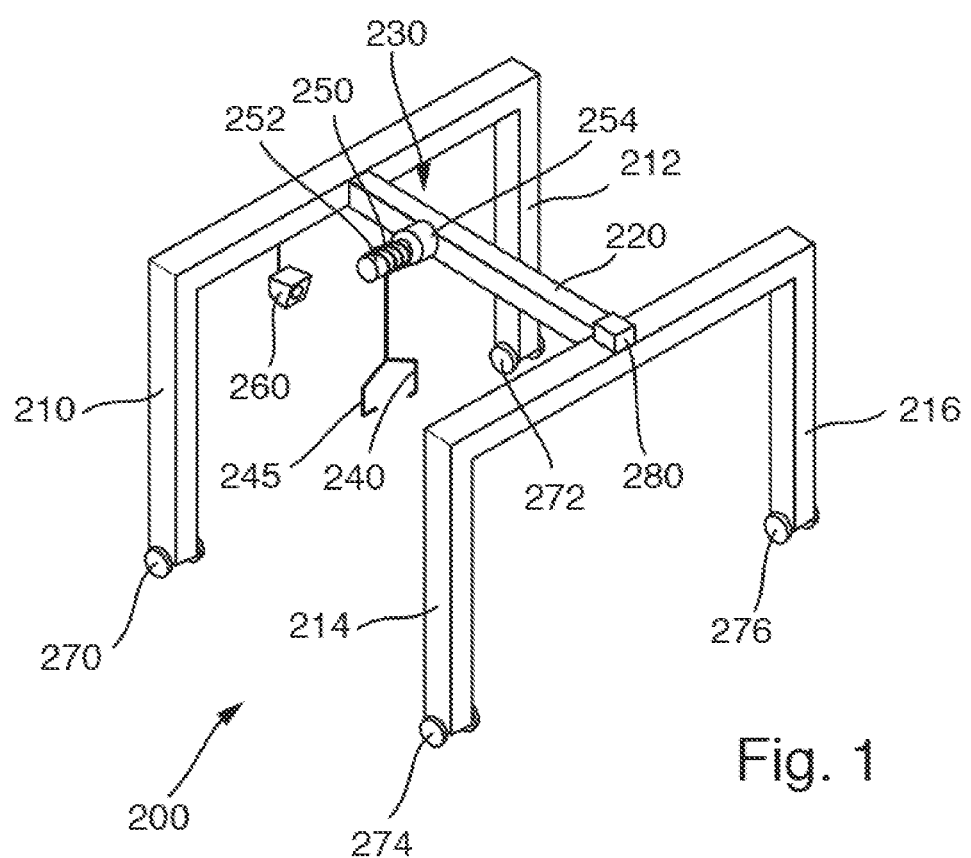
FIG. 1 illustrates schematically a recovery device according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

The present disclosure relates to a laboratory sample distribution system. The laboratory sample distribution system can comprise a plurality of sample container carriers adapted to carry one or more sample containers, a transport plane adapted to support the sample container carriers, a movement device adapted to move a sample container carrier on top of the transport plane, a control device configured to control the movement of the sample container carriers on top of the transport plane by controlling the movement device such that the sample container carriers move along corresponding transport paths, and a recovery device. The recovery device can comprise a handler adapted to handle a sample container carrier or a sample container, and a drive adapted to move the recovery device on the transport plane.

By use of the recovery device, it can be possible to handle a sample container carrier or a sample container if an error condition has occurred. For example, if a sample container carrier cannot be moved by the movement device or the drive such as electromagnetic actuators, as will be described in further detail below, the recovery device can provide for a controlled movement of the sample container carrier. No manual action may be needed. The recovery device can furthermore be equipped with specific handler in order to perform certain tasks, as will be described in further detail below. The recovery device and/or a different part of the laboratory sample distribution system and/or the control device can also be equipped with specific sensors in order to fully or partially automatically recognize a specific situation and determine what action has to be taken in order to bring the laboratory sample distribution system in condition for further operation. The different part may be a stationary part of the laboratory sample distribution system, for example, a cover housing for the transport plane with the sample container carriers. In detail, the recovery device and/or the different part of the laboratory sample distribution system and/or the control device may comprise a control unit adapted to control the handler and/or the drive of the recovery device, in particular, a controlled movement of the handler. The control unit may be logically coupled to the specific sensors or be a part of them such that the control unit can be adapted to fully or partially automatically recognize a specific situation and determine what action has to be taken in order to bring the laboratory sample distribution system in condition for further operation.

Sample containers can typically be implemented as tubes made of transparent glass or plastic. Such sample containers can be easily put in a sample container carrier for transport between laboratory stations.

The transport plane can also be denoted as a transport surface. Typically, it can be possible to move the sample container carriers in two dimensions on top of the transport plane. This can provide for a great flexibility in bringing the sample container carriers to specific positions.

The handler can be adapted to perform tasks like grabbing, lifting from the transport plane, rotating, pushing, pulling or other kinds of movement or handling. Specific implementations of the handler will be discussed in greater detail below.

It should be noted that a recovery device may also be adapted such that it can be able to handle a plurality of sample container carriers or sample containers in parallel. This can diminish a time needed for a recovery operation.

According to one embodiment, each sample container carrier can comprise at least one energy source to furnish drive power such as, for example, a battery and/or an induction coil, at least one movement device such as, for example, a wheel, with which the sample container carrier can move independently on the transport plane, and at least one drive device such as, for example, an electric motor, to drive the at least one movement device. The at least one drive device can be driven by the drive power. The energy source, the at least one movement device and the at least one drive device can form the movement device and the control device can be configured to control the movement of the sample container carriers on top of the transport plane by controlling or driving the energy sources and/or the drive devices such that the sample container carriers move along corresponding transport paths.

In addition the laboratory sample distribution system may comprise at least one complementary energy source adapted to provide the energy sources of the sample container carriers with energy. The at least one complementary energy source may be stationary arranged above or below the transport plane. The control device may be configured to control the at least one complementary energy source in order to control the energy provision of the energy sources of the sample container carriers. For example, the at least one complementary energy source may comprise a charging station adapted to charge the batteries of the sample container carriers. Additionally or alternatively, the at least one complementary energy source may comprise at least one induction coil adapted to transfer energy to the induction coils of the sample container carriers.

According to one embodiment, each sample container carrier can comprise at least one magnetically active device, for example, in the form of a permanent magnet. The movement device can comprise a plurality of electromagnetic actuators stationary arranged below the transport plane. The electromagnetic actuators can be adapted to move a sample container carrier on top of the transport plane by applying a magnetic force to the sample container carrier. The control device can be configured to control the movement of the sample container carriers on top of the transport plane by driving the electromagnetic actuators such that the sample container carriers can move along corresponding transport paths.

The sample container carriers can typically move on top of the transport plane by the magnetic force applied using the electromagnetic actuators. As the electromagnetic actuators can typically be in a quite close proximity to each other, the control device can control movement of the sample container carriers easily.

The drive can be adapted to move the recovery device on the transport plane by making use of the same transport principle as the sample container carriers. Additionally or alternatively, the drive can be adapted to move the recovery device on the transport plane independently, i.e. self-driven. With the latter implementation, it can be possible to move the recovery device on the transport plane even if, for example, the electromagnetic actuators or the control device are out of service.

The drive may comprise at least one magnetically active element adapted to interact with at least one electromagnetic actuator such that a magnetic drive force can be applied to the recovery device. The magnetically active element may be adapted to interact with a magnetic field of the electromagnetic actuators. The magnetically active element may be a permanent magnet or an electromagnet or a combination thereof. The recovery device may be driven on the transport plane using the same drive principles as used for the sample container carriers, i.e. using the electromagnetic actuators arranged below the transport plane.

The drive may also comprise an electromagnet that may have a ferromagnetic core.

The magnetically active element may comprise an electromagnetic actuator. This can allow for a controlled application of a magnetic field by the recovery device, for example in order to be moved on the transport plane or to actively move on the transport plane. It can be noted that in some arrangements a combination of electromagnetic actuators in the recovery device, energized and de-energized in a certain way, may lead to a specific movement of the recovery device on the transport plane. Therefore, the electromagnetic actuators of the recovery device can be arranged in a distance between each other that is different from the distance between the electromagnetic actuators of the laboratory sample distribution system.

According to one embodiment, the drive can be adapted to move the recovery device on the transport plane independent from the movement device such as, for example, the electromagnetic actuators, of the laboratory sample distribution system, thus increasing the flexibility of the recovery device.

For example, the drive may comprise a plurality of wheels or chains and a plurality of electric motors for driving the wheels or chains. By such wheels or chains, the recovery device may move on the transport plane like a car. For example, the wheels or chains may be driven in order to move the recovery device forward and the wheels may be steered in order to control the direction in which this recovery device moves. Alternatively, the wheels or chains may be driven differentially in order to control the direction in which the recovery device moves.

According to one embodiment, the recovery device can comprise a communicator for communicating with the control device such that the recovery device can be remote controllable by the control device. The control device may send drive commands to the recovery device in order to direct the recovery device to a location where action by the recovery device is needed.

By use of the communicator, the control device can control movement of the recovery device over the transport plane using the drive. Thus, the control device can control the recovery device in addition to controlling the sample container carriers. Additionally, by use of the communicator, the control device may control the handler of the recovery device.

According to one embodiment, the handler can comprise a rod adapted to mechanically couple a sample container carrier or a sample container to the recovery device. The rod may be equipped with a rake at an end of the rod. Using such a rod, the recovery device may, for example, mechanically push or pull a sample container carrier that is unable to move on its own. This allows for evacuation of such a sample container carrier from the transport plane by use of the recovery device.

The rod may be retractable and/or foldable. Especially, retracting and/or folding the rod may be done automatically, e.g. responsive to a command received from the control device. In this embodiment, the rod may only be brought into a working position when a sample container carrier is actually to be connected, and does not restrict movement of the recovery device if not needed.

According to one embodiment, the handler can comprise a crane device positionable over a sample container carrier and/or a sample container and can be adapted to grab and collect the sample container carrier and/or the sample container. Thus, the recovery device may move the sample container carrier or the sample container over the transport plane which can e.g. be done even if the sample container carrier or the sample container are in a position in which normal movement may not be possible. Such a situation can, for example, arise due to the sample container carrier or the sample container being in a tilted position or damaged.

According to one embodiment, the crane device can comprise a claw being movable up and down. Such a claw can especially be used in order to grab and collect an item. It can be moved down in order to grab the item from its lower side, the claw may be tilted or moved horizontally in order to move at least partially below the item, and the item may be moved up together with the claw.

According to one embodiment, the recovery device and/or a different part of the laboratory sample distribution system and/or the control device can comprise an environment scanner adapted to: recognize a sample container carrier and/or a sample container, and/or determine if a sample container is contained in a sample container carrier, and/or determine if a sample container carrier and/or a sample container has tilted over, and/or determine if a sample container carrier and/or a sample container is contaminated.

The different part may be a stationary part of the laboratory sample distribution system, such as, for example, a cover housing for the transport plane with the sample container carriers. The environment scanner may comprise or be logically coupled to the before mentioned control unit.

With such an environment scanner, it can be possible for the recovery device and/or the different part and/or the control device to autonomously determine a situation of a sample container carrier or a sample container, e.g. to autonomously determine what kind of fault has occurred and what action can be done. For example, the sample container carrier or the sample container may be recognized in order to grab and collect the sample container carrier or the sample container. Position and presence of a sample container or a sample container carrier may be determined in order to control recovery actions. A contamination may be detected in order to determine if a sample container carrier or a sample container may further move on the transport plane, or if the sample container carrier or the sample container have to be put temporarily out of service in order to avoid the risk of further spreading the contamination. Further, the contaminated parts of the transport plane may be set (temporarily) out of service.

In typical implementations, the environment scanner can comprise one or more of the following components: a camera, a magnetic sensor, an RFID receiver, an ultrasonic sensor, and a haptic sensor. These environment scanners can be used in order to assist the recovery device in managing typical fault situations in which its action may be required.

By use of the inventive laboratory sample distribution system, the afore-mentioned advantages of a recovery device can be utilized for a laboratory sample distribution system. The statements given with respect to the laboratory sample distribution system when discussing the recovery device above apply accordingly to the inventive laboratory sample distribution system. Regarding the recovery device for the laboratory sample distribution system, all implementations and variations as discussed above can be used. Mentioned advantages apply accordingly.

In one embodiment, a plurality of fields can be defined on the transport plane in a checkered manner. Each electromagnetic actuator can be located below one of these fields such that in each second line of fields, each second field is left blank, and each sample container carrier can extend over one field. This arrangement of electromagnetic actuators can be advantageously in practice. A line having no blanks can be used as transport line on which sample container carriers move. The neighboring lines having blanks can provide for a certain distance to nearby moving sample container carriers.

In one embodiment, the recovery device can extend over three fields in width and three fields in lengths. This can provide for a sufficient stabilization of the recovery device and further can provide for the possibility to move the recovery device such that a sample container carrier can be positioned under elements of the recovery device. This can allow, for example, for operation of the crane device mentioned above.

In one embodiment, the recovery device can have four stilts arranged such that each stilt can abut one field and that the stilts can carry a horizontal beam extending over at least one field such that a sample container carrier having a sample container comprised in the sample container carrier can be placed below the beam. This implementation can allow, for example, for moving the recovery device over a sample container carrier and a sample container that is to be handled. For example, the above-mentioned crane device can be fixed at the beam and can be moved down from the beam.

The present disclose can further relate to a laboratory automation system, comprising a plurality, e.g., two or more, of a pre-analytical, analytical and/or post-analytical (laboratory) stations, and a laboratory sample distribution system as described above adapted to transport the sample container carriers and/or sample containers between the stations. The stations may be arranged adjacent to the laboratory sample distribution system.

Pre-analytical stations may be adapted to perform any kind of pre-processing of samples, sample containers and/or sample container carriers.

Analytical stations may be adapted to use a sample or part of the sample and a reagent to generate a measuring signal, the measuring signal indicating if and in which concentration, if any, an analyte is existing.

Post-analytical stations may be adapted to perform any kind of post-processing of samples, sample containers and/or sample container carriers.

The pre-analytical, analytical and/or post-analytical stations may comprise at least one of a decapping station, a recapping station, an aliquot station, a centrifugation station, an archiving station, a pipetting station, a sorting station, a tube type identification station, and a sample quality determining station.

Referring initially to FIG. 1, FIG. 1 shows a recovery device 200. The recovery device 200 can comprise four stilts, namely a first stilt 210, a second stilt 212, a third stilt 214 and a fourth stilt 216. The first stilt 210 and the second stilt 212 can be mechanically coupled by a first horizontal bearing. The first stilt 210, the second stilt 212 and the first horizontal bearing can form an inverse U. Accordingly, the third stilt 214 and the fourth stilt 216 can be mechanically coupled by a second horizontal bearing. The third stilt 214, the fourth stilt 216 and the second horizontal bearing can form an inverse U. The inverse U can be understood such that the U is opened to the bottom.

Between the horizontal bearings coupling the stilts 210, 212 and 214, 216, respectively, a beam 220 can be arranged. The beam 220 can connect the two U-shaped arrangements of the stilts 210, 212, 214, 216 including the horizontal bearings. Thus, a space can be provided below the beam 220. Between two neighboring stilts 210, 212, 214, 216, a space can be left blank so that the recovery device 200 can move over an item being positioned on a transport plane.

A handler in the form of a crane device 230 can be arranged at the beam 220. The crane device 230 can comprise a first claw 240 and a second claw 245. The two claws 240, 245 together can form a grabber. The two claws 240, 245 can be attached to a cable 250. The cable 250 can be wound on a cable drum 252, which can also be attached to the beam 220. The cable drum 252 can be functionally coupled to an electric motor 254. The electric motor 254 can rotate the cable drum 252, so that the claws 240, 245 can be moved up and down. The claws 240, 245 can also be moved sidewise, i.e., parallel to a transport plane on which the recovery device 200 is moving.

The recovery device 200 can further comprise four pairs of wheels, such that the recovery device 200 can be moved autonomously on a transport plane. A first pair of wheels 270 can be arranged at the bottom of the first stilt 210. A second pair of wheels 272 can be arranged at the bottom of the second stilt 212. A third pair of wheels 274 can be arranged at the bottom of the third stilt 214. A fourth pair of wheels 276 can be arranged at the bottom of the fourth stilt 216. With the pairs of wheels 270, 272, 274, 276, it can be possible to propel the recovery device 200 over a transport plane. For controlling a direction of movement, different angular velocities of the pairs of wheels 270, 272, 274, 276 can be set.

The recovery device 200 can further comprise a camera 260 directed to a position under the claws 240, 245. This can allow the recovery device 200 to determine a situation, for example, to see a sample container carrier and/or a sample container on the transport plane and to determine which action can be taken in order to recover the sample container carrier and/or the sample container.

The recovery device 200 can further comprise a communicator or a control unit or a control device 280. The control unit 280 can wirelessly communicate with a control device of a laboratory sample distribution system, which will be described further below with reference to FIG. 2. From the control device of the laboratory sample distribution system, the control unit 280 can receive drive commands such that the recovery device 200 can be remote controllable by the control device. The control unit 280 can control respective angular velocities of the wheels 270, 272, 274, 276 such that the recovery device 200 can move to a position as set by the control device.

When the recovery device 200 arrives at a position at which an error condition has occurred, the camera 260 can generate picture data regarding the condition in which a sample container carrier or a sample container is. For example, the camera 260 may determine that a sample container and a sample container carrier have been tilted over, which can be a situation in which recovery action can be performed. The control unit 280 can receive respective image information from the camera 260 in order to make such a determination.

When the control unit 280 is aware of the situation, it can move the recovery device 200 just over any item that can be recovered, can move the claws 240, 245 down so that they can grab the item, can move the claws 240, 245 horizontally such that the item can actually be grabbed, and can move the claws 240, 245 up in the direction of the beam 220. In such a condition, the recovery device 200 may bring the item to a safe location, for example to an edge of a transport plane in order to remove the item.

FIG. 2 shows a laboratory sample distribution system 100 according to an embodiment. The laboratory sample distribution system 100 can be part of a laboratory automation system 10 according to an embodiment, which can further comprise a first laboratory station 20 and a second laboratory station 30.

The laboratory sample distribution system 100 can comprise a transport plane 110. Below the transport plane 110, a plurality of electromagnetic actuators 120 can be arranged. Each electromagnetic actuator 120 can comprise a ferromagnetic core 125. The electromagnetic actuators 120 can be arranged in fields configured in a checkered manner. In each second line of fields, each second position can be left blank. Each other field can have one electromagnetic actuator 120.

Sample container carriers 140, 147 can be placed on top of the transport plane 110. The sample container carriers 140, 147 can carry a respective sample container 145 and 148. In a fault free condition, each sample container carrier 140, 147 can extend over one field. It can be understood that typically more than two sample container carriers can be arranged on top of the transport plane 110.

The transport plane 110 can further comprise a plurality of Hall-sensors 130 that can be used in order to determine the position of a sample container carrier 140, 147.

Each sample container carrier 140, 147 can comprise a magnetically active element in the form of a permanent magnet to interact with a magnetic field generated by the electromagnetic actuators 120. In this manner, the sample container carriers 140, 147 can be moved over the transport plane 110.

The laboratory sample distribution system 100 can further comprise a control device 150 to control the electromagnetic actuators 120. The control device 150 can energize and de-energize the electromagnetic actuators 120. Thus, the control device 150 can control movement of the sample container carriers 140, 147. The control device 150 can move the sample container carriers 140, 147 along specific paths, e.g. to one of the analyzers 20, 30.

As depicted, the sample container carrier 147 can be tilted over. Such an error condition can occur due to accidents, for example, at occurrence of an earthquake. To address such an error condition, the laboratory sample distribution system 100 can comprise the recovery device 200 as described above with reference to FIG. 1.

The recovery device 200 can move independently on the transport plane 110 using its wheels 270, 272, 274, 276. In the current situation, the recovery device 200 can move to the left side of the transport plane 110 and can grab and collect both the tilted over sample container carrier 147 and the tilted over sample container 148. Thus, the recovery device 200 can put the laboratory sample distribution system 100 in an error-free condition for further operation despite the occurrence of the accident, without the need of manual interaction. It is noted that the recovery device 200 can extend over three fields in length and three fields in width.

The camera 260 of the recovery device 200 can detect that a blood contamination 149 has occurred on the transport plane 110 due to the tilted over sample container 148 in which a blood sample was contained. Thus, the control unit 280 of the recovery device 200 may ensure that the recovery device 200 does not move over the blood contamination 149, so that no contamination can be spread over the transport plane (110).

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

I claim:

1. A laboratory sample distribution system, the laboratory sample distribution system comprising:
   a plurality of sample container carriers to carry one or more sample containers;
   a transport surface to support the sample container carriers;
   a movement device to move the sample container carriers on top of the transport surface, wherein the movement device comprises a plurality of electro-magnetic actuators arranged stationary below the transport surface, the electro-magnetic actuators move the sample container carriers on top of the transport surface by applying a magnetic force to the sample container carriers;
   a control device programmed to control the movement of the sample container carriers on top of the transport surface by controlling the movement device such that the sample container carriers move along corresponding transport paths;
   a recovery device, wherein the recovery device comprises:
      a handler to handle a sample container carrier or a sample container, wherein the handler comprises a crane device comprising a claw, the handler positionable over a sample container carrier and/or a sample container to grab and collect the sample container carrier and/or the sample container, and
      a drive to move the recovery device on top of the transport surface, wherein the drive comprises at least one magnetically active element adapted to interact with at least one electro-magnetic actuator of the movement device such that a magnetic drive force is applied to the recovery device, and wherein the transport surface supports the recovery device; and
   wherein the control device is programmed to control the movement of the recovery device on top of the transport surface by controlling the at least one electro-magnetic actuator of the movement device to apply the magnetic drive force to the magnetically active element of the recovery device.

2. The laboratory sample distribution system according to claim 1, wherein each sample container carrier comprises at least one magnetically active device.

3. The laboratory sample distribution system according claim 1, wherein the drive moves the recovery device on top of the transport surface independent from the movement of the sample container carriers.

4. The laboratory sample distribution system according to claim 1, wherein the recovery device further comprises,
   a control unit for communicating with the control device such that the recovery device is remote controllable by the control device.

5. The laboratory sample distribution system according to claim 1, wherein the claw is vertically movable.

6. The laboratory sample distribution system according to claim 1, wherein the recovery device comprises a camera to:
   recognize a sample container carrier and/or a sample container and/or
   determine if a sample container is contained in a sample container carrier and/or
   determine if a sample container carrier and/or a sample container has tilted over and/or
   determine if a sample container carrier and/or a sample container is contaminated.

7. The laboratory sample distribution system according to claim 1, wherein a number of fields is defined on the transport surface in a checkered manner, wherein the electromagnetic actuators are located below a corresponding one of the fields such that the actuators are arranged in the checkered manner.

8. The laboratory sample distribution system according to claim 7, wherein each sample container carrier extends over one of the fields.

9. The laboratory sample distribution system according to claim 8, wherein the recovery device extends over three fields in width and three fields in length.

10. The laboratory sample distribution system according to claim 9, wherein the recovery device has four stilts arranged such that each stilt abuts one field, wherein the stilts carry a horizontal beam extending over at least one field.

11. A laboratory automation system, the laboratory automation system comprising:
    a plurality of laboratory stations; and
    the laboratory sample distribution system according to claim 1 to distribute sample container carriers between the laboratory stations.

12. The laboratory automation system according to claim 11, wherein the plurality of laboratory stations are in the form of pre-analytical, analytical and/or post-analytical stations.

* * * * *